United States Patent
Balthasart et al.

(10) Patent No.: US 7,863,490 B2
(45) Date of Patent: *Jan. 4, 2011

(54) PROCESS FOR THE MANUFACTURE OF 1,2-DICHLOROETHANE

(75) Inventors: Dominique Balthasart, Brussels (BE); Michel Strebelle, Brussels (BE); Michel Lempereur, Corbais (BE)

(73) Assignee: Solvay (Société Anonyme), Brussels (BE)

( * ) Notice: Subject to any disclaimer, the term of this patent is extended or adjusted under 35 U.S.C. 154(b) by 213 days.

This patent is subject to a terminal disclaimer.

(21) Appl. No.: 11/722,589

(22) PCT Filed: Dec. 21, 2005

(86) PCT No.: PCT/EP2005/057045

§ 371 (c)(1),
(2), (4) Date: Oct. 18, 2007

(87) PCT Pub. No.: WO2006/067190

PCT Pub. Date: Jun. 29, 2006

(65) Prior Publication Data

US 2008/0207966 A1    Aug. 28, 2008

(30) Foreign Application Priority Data

Dec. 23, 2004  (FR) ................................. 04 13873
Apr. 1, 2005   (FR) ................................. 05 03252
Apr. 1, 2005   (FR) ................................. 05 03254

(51) Int. Cl.
*C07C 17/00* (2006.01)

(52) U.S. Cl. ........................ 570/224; 570/225; 570/244; 562/62

(58) Field of Classification Search ................. 570/224, 570/225; 526/62

See application file for complete search history.

(56) References Cited

U.S. PATENT DOCUMENTS 5,488,190 A * 1/1996 Le Blevec et al. ........... 570/226

(Continued)

FOREIGN PATENT DOCUMENTS

BE          707 370            4/1968

(Continued)

OTHER PUBLICATIONS

Bhatnagar, R.K., Selection of a process for manufacture of ethylene dichloride, 1966, Shri Ram Inst. Ind. Res., Delhi Chemical Age of India, 17(7) pp. 521-524 (1 page abstract).*

(Continued)

*Primary Examiner*—Jafar Parsa
*Assistant Examiner*—Yate' K Cutliff
(74) *Attorney, Agent, or Firm*—Oblon, Spivak, McClelland, Maier & Neustadt, L.L.P.

(57) ABSTRACT

Process for the manufacture of 1,2-dichloroethane starting with a hydrocarbon source according to which: a) the hydrocarbon source is subjected to cracking which produces a mixture of products containing ethylene and other constituents; b) the mixture of products containing ethylene is conveyed to at least one storage reservoir; c) a chlorination reactor and/or an oxychlorination reactor is (are) supplied with the previously stored mixture of products containing ethylene, in which reactors most of the ethylene present is converted to 1,2-dichloroethane; d) the 1,2-dichloroethane obtained is separated from the streams of products derived from the chlorination and oxychlorination reactors.

20 Claims, 1 Drawing Sheet

U.S. PATENT DOCUMENTS

| | | | | |
|---|---|---|---|---|
| 5,789,499 | A | * | 8/1998 | Masuko et al. ............... 526/62 |
| 6,437,204 | B1 | | 8/2002 | Benje et al. |
| 6,907,293 | B2 | | 6/2005 | Grill et al. |
| 7,311,813 | B2 | * | 12/2007 | Reyneke et al. ............ 208/102 |
| 2007/0142682 | A1 | | 6/2007 | Strebelle et al. |
| 2007/0161830 | A1 | | 7/2007 | Strebelle |

FOREIGN PATENT DOCUMENTS

| | | |
|---|---|---|
| EP | 0 567 381 | 10/1993 |
| GB | 1 207 767 | 5/1969 |
| WO | 00 26164 | 5/2000 |
| WO | 03 048088 | 6/2003 |

OTHER PUBLICATIONS

U.S. Appl. No. 12/304,297, filed Dec. 11, 2008, Balthasart, et al.
U.S. Appl. No. 12/304,329, filed Dec. 11, 2008, Strebelle, et al.
U.S. Appl. No. 12/304,379, filed Dec. 11, 2008, Balthasart, et al.
U.S. Appl. No. 12/304,434, filed Dec. 11, 2008, Strebelle, et al.
Apr. 5, 2007 Office Action, issued by the U.S. Patent and Trademark Office, in connection with U.S. Appl. No. 10/488,334.
Apr. 25, 2008 Office Action, issued by the U.S. Patent and Trademark Office, in connection with U.S. Appl. No. 10/488,334.
Van den Hoert et al., (1979) "Generation of unidirectionally propogated action potentials in a peripheral nerve brief stim uli", Science, vol. 206: 1311-1312.
J. L. Koolen, "Optimization of an Integrated Complex of Process Plants and Evaluation of its Vulnerability", Design of Simple and Robust Process Plants, XP 002378101, pp. 251-282, 2002.
Heinz Zimmermann, et al., "Ethylene", Ullmann'S Encyclopedia of Industrial Chemistry, XP 002356911, pp. 1-47, 2000.
U.S. Appl. No. 11/722,587, filed Jun. 22, 2007, Strebelle, et al.
U.S. Appl. No. 11/722,603, filed Jun. 22, 2007, Strebelle, et al.
U.S. Appl. No. 11/722,598, filed Jun. 22, 2007, Strebelle, et al.
U.S. Appl. No. 11/722,607, filed Jun. 22, 2007, Strebelle, et al.

* cited by examiner

PROCESS FOR THE MANUFACTURE OF 1,2-DICHLOROETHANE

This application is a 371 of PCT/EP05/57045, filed Dec. 21, 2005.

The present invention relates to a process for the manufacture of 1,2-di-chloroethane (DCE), a process for the manufacture of vinyl chloride (VC) and a process for the manufacture of polyvinyl chloride (PVC).

To date, ethylene which is more than 99.8% pure is normally used for the manufacture of DCE essentially intended for the manufacture of VCM. This ethylene of very high purity is obtained via the cracking of various petroleum products, followed by numerous complex and expensive separation steps in order to isolate the ethylene from the other products of cracking and to obtain a product of very high purity.

Given the high cost linked to the production of ethylene of such high purity, various processes for the manufacture of DCE using ethylene having a purity of less than 99.8% have been developed. These processes have the advantage of reducing the costs by simplifying the course of separating the products resulting from the cracking and by thus abandoning complex separations which are of no benefit for the manufacture of DCE.

For example, patent application WO 00/26164 describes a process for the manufacture of DCE by simplified cracking of ethane coupled with chlorination of ethylene. To this effect, an ethylene chlorination step takes place in the presence of the impurities obtained during the cracking of the ethane.

Patent application WO 03/48088 describes, for its part, a process for the manufacture of DCE by dehydrogenation of ethane, giving rise to the formation of a fraction comprising ethane, ethylene and impurities including hydrogen, which fraction is then subjected to chlorination and/or oxychlorination.

While in a conventional unit for the production of DCE by chlorination and/or oxychlorination of ethylene which is more than 99.8% pure, an ethylene supply is generally available which is obtained from a network of pipelines which itself constitutes an important buffer capacity which makes it possible to modulate the flow rate of ethylene and thereby ensure good operation of the chlorination and/or oxychlorination reactors, the rate of production of ethylene in the processes described which involve ethylene of lower purity produced in the integrated unit itself is essentially controlled by the operation of the oven for cracking the hydrocarbon source. These ovens have a production imposed by their soiling and by the succession of decocking operations. Fluctuations in the quality and the quantity of the load to be cracked are also sources of variation of the quantity of ethylene. For these reasons, it is difficult to carry out these crackings in order to obtain therefrom a stable rate of production of ethylene and therefore to regulate their production in real time. The consequence of this is that it is thus difficult to control the good operation of the chlorination and/or oxychlorination reactors which are directly linked thereto.

The aim of the present invention is therefore to provide a process using ethylene with a purity of less than 99.8% which has the advantage of reducing the costs by abandoning complex separations for isolating the ethylene from the other products of cracking which are of no benefit for the manufacture of DCE, and which has the advantage of avoiding the abovementioned problems while making it possible to modulate the flow rate of ethylene and thus to ensure the good operation of the chlorination and/or oxychlorination reactors.

To this effect, the invention relates to a process for the manufacture of 1,2-dichloroethane starting with a hydrocarbon source according to which:
a) the hydrocarbon source is subjected to cracking which produces a mixture of products containing ethylene and other constituents;
b) the mixture of products containing ethylene is conveyed to at least one storage reservoir;
c) a chlorination reactor and/or an oxychlorination reactor is (are) supplied with the previously stored mixture of products containing ethylene, in which reactors most of the ethylene present is converted to 1,2-dichloroethane;
d) the 1,2-dichloroethane obtained is separated from the streams of products derived from the chlorination and oxychlorination reactors.

The hydrocarbon source considered may be any known hydrocarbon source. Preferably, the hydrocarbon source subjected to cracking (step a)) is chosen from the group consisting of naphtha, gas oil, natural gas liquid, ethane, propane, butane, isobutane and mixtures thereof. In a particularly preferred manner, the hydrocarbon source is chosen from the group consisting of ethane, propane and propane/butane mixtures. Good results were obtained with a hydrocarbon source chosen from the group consisting of propane and propane/butane mixtures. The propane/butane mixtures may exist as such or may consist of mixtures of propane and butane.

The expression ethane, propane, butane and propane/butane mixtures is understood to mean, for the purposes of the present invention, products that are commercially available, namely that consist mainly of the pure product (ethane, propane, butane or propane/butane as a mixture) and secondarily of other saturated or unsaturated hydrocarbons, which are lighter or heavier than the pure product itself.

The expression cracking (step a)) is understood to mean, for the purposes of the present invention, all the steps for treating the hydrocarbon source which lead to the formation of a mixture of products containing ethylene and other constituents.

Such a cracking may be carried out according to any known technique as long as it allows the production of a mixture of products containing ethylene and other constituents. Advantageously, the cracking comprises a first step of pyrolysis (that is to say a conversion under the action of heat) of the hydrocarbon source in the presence or absence of third compounds such as water, oxygen, a sulphur derivative and/or a catalyst. This first step is preferably followed by steps for thermal recovery of the heat of the cracked gases, for separating the heavy products (for example via organic quenching and aqueous quenching), for compressing and drying the gases and for removing most of the carbon dioxide and most of the sulphur compounds present or added (for example by means of an alkaline wash), optionally for hydrogenating the undesirable derivatives such as for example acetylene and optionally the removal of part of the hydrogen and/or of the methane, for example via a PSA (pressure swing adsorption) process or via a membrane process.

Advantageously, in the process according to the invention, the mixture of products containing ethylene and other constituents derived from step a) comprises hydrogen, methane, compounds comprising from 2 to 7 carbon atoms, carbon monoxide, nitrogen and oxygen. The hydrogen, the methane and the compounds comprising from 2 to 7 carbon atoms other than acetylene are preferably present in an amount of at least 200 ppm by volume relative to the total volume of the said mixture of products. The carbon monoxide, the nitrogen, the oxygen and the acetylene may be present in an amount of less than 200 ppm by volume or in an amount of at least 200 ppm by volume relative to the total volume of the said mixture of products. Compounds containing more than 7 carbon atoms, carbon dioxide, hydrogen sulphide and other sulpho compounds and water may also be present in the abovementioned mixture of products in an amount of less than 200 ppm by volume relative to the total volume of the said mixture of products.

The expression storage reservoir is understood to mean, for the purposes of the present invention, any container in which the mixture of products containing ethylene is stored while waiting to be used.

According to a preferred variant, the process according to the invention is characterized in that after step a) and before step d):

b1) the mixture of products containing ethylene is separated into a fraction enriched with the compounds lighter than ethylene containing part of the ethylene (fraction A), into a fraction enriched with ethylene (fraction B) and into a heavy fraction (fraction C);

b2) fraction A and fraction B are conveyed to separate storage reservoirs (storage reservoir A or reservoir A and storage reservoir B or reservoir B, respectively); and c) the fraction A stored in reservoir A is conveyed to a chlorination reactor while fraction B stored in reservoir B is conveyed to a chlorination reactor and/or an oxychlorination reactor, in which reactors most of the ethylene present is converted to 1,2-dichloroethane.

According to the process of the invention, the quantities defined below to characterize the fraction B and the fraction A are those before their respective entry into chlorination/oxychlorination and into chlorination.

According to the preferred variant of the process according to the invention, fraction B containing part of the ethylene is enriched with ethylene. Fraction B is advantageously characterized by a hydrogen content of less than or equal to 2%, preferably of less than or equal to 0.5% and in a particularly preferred manner of less than or equal to 0.1% by volume relative to the total volume of fraction B.

Fraction B is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction B.

Fraction B advantageously contains from 40% to 99.5% by volume of ethylene relative to the total volume of fraction B. Fraction B advantageously contains at least 40%, preferably at least 50% and in a particularly preferred manner at least 60% by volume of ethylene relative to the total volume of fraction B. Fraction B advantageously contains at most 99.5%, preferably at most 99.2% and in a particularly preferred manner at most 99% by volume of ethylene relative to the total volume of fraction B.

In the preferred case where the hydrocarbon source is ethane, fraction B advantageously comprises at least 60%, preferably at least 70% and in a particularly preferred manner at least 75% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

In the preferred case where the hydrocarbon source is a propane/butane mixture, fraction B advantageously comprises at least 40%, preferably at least 50% and in a particularly preferred manner at least 60% by volume of ethylene relative to the total volume of fraction B. Fraction B advantageously comprises at most 99.5%, preferably at most 99.2% and in a particularly preferred manner at most 99% by volume of ethylene relative to the total volume of fraction B.

Fraction B is additionally characterized by an acetylene content which is advantageously less than or equal to 0.01%, preferably less than or equal to 0.005% and in a particularly preferred manner less than or equal to 0.001% by volume relative to the total volume of fraction B.

According to the preferred variant of the process according to the invention, fraction B is conveyed to a chlorination reactor and/or an oxychlorination reactor, preferably with energy recovery.

According to the preferred variant of the process according to the invention, fraction A containing part of the ethylene is enriched with compounds which are lighter than ethylene. These compounds are generally methane, nitrogen, oxygen, hydrogen and carbon monoxide. Advantageously, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.97% and in a particularly preferred manner at most 99.95% of compounds lighter than ethylene which are contained in the mixture of products subjected to step b).

In the preferred case where the hydrocarbon source is ethane, fraction A contains at least 90%, preferably at least 95% and in a particularly preferred manner at least 98% of compounds lighter than ethylene which are contained in the mixture of products subjected to step b). Advantageously, fraction A contains at most 99.99%, preferably at most 99.98% and in a particularly preferred manner at most 99.97% of compounds lighter than ethylene which are contained in the mixture of products subjected to step b).

In the preferred case where the hydrocarbon source is a propane/butane mixture, fraction A contains at least 70%, preferably at least 80% and in a particularly preferred manner at least 85% of compounds lighter than ethylene which are contained in the mixture of products subjected to step b). Advantageously, fraction A contains at most 99.99%, preferably at most 99.95% and in a particularly preferred manner at most 99.9% of compounds lighter than ethylene which are contained in the mixture of products subjected to step b).

Fraction A is characterized by a content of compounds containing at least 3 carbon atoms, advantageously less than or equal to 0.01%, preferably less than or equal to 0.005% and in a particularly preferred manner less than or equal to 0.001% by volume relative to the total volume of fraction A.

Fraction A advantageously contains a content by volume of ethylene such that it represents from 10% to 90% of the content by volume of ethylene of fraction B. Fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

In the preferred case where the hydrocarbon source is ethane, fraction A advantageously contains a content by volume of ethylene such that it is less than or equal to 90%, preferably less than or equal to 85% and in a particularly preferred manner less than or equal to 80% of the content by volume of ethylene of fraction B. Fraction A advantageously contains a content by volume of ethylene such that it is at least 15%, preferably at least 20% and in a particularly preferred manner at least 22% of the content by volume of ethylene of fraction B.

In the preferred case where the hydrocarbon source is a propane/butane mixture, fraction A advantageously contains a content by volume of ethylene such that it is less than or equal to 80%, preferably less than or equal to 75% and in a particularly preferred manner less than or equal to 70% of the content by volume of ethylene of fraction B. Fraction A advantageously contains a content by volume of ethylene such that it is at least 10%, preferably at least 15% and in a particularly preferred manner at least 20% of the content by volume of ethylene of fraction B.

Fraction A is additionally characterized by an acetylene content which is advantageously less than or equal to 0.01%, preferably less than or equal to 0.005% and in a particularly preferred manner less than or equal to 0.001% by volume relative to the total volume of fraction A.

According to the preferred variant of the process according to the invention, fraction A is conveyed to a chlorination reactor, preferably after expansion with recovery of energy.

According to a first subvariant of the preferred variant of the process according to the invention, considering that the process for the manufacture of DCE is advantageously balanced (that is to say that the process of manufacture by chlorination and oxychlorination of ethylene and pyrolysis of the 1,2-di-chloroethane (DCE) formed makes it possible to generate the quantity of HCl necessary for the process), the fraction by weight of the ethylene throughput in each of fractions A and B is advantageously between 45 and 55% of the total quantity of ethylene produced (fraction A+fraction B). Preferably, the fraction by weight of the throughput of ethylene in fraction A is of the order of 55% and the fraction by weight of the throughput of ethylene in fraction B is of the order of 45% of the total quantity produced. In a particularly preferred manner, the fraction by weight of the throughput of ethylene in fraction A is of the order of 52.5% and the fraction by weight of the throughput of ethylene in fraction B is of the order of 47.5% of the total quantity produced.

According to a second subvariant of the preferred variant of the process according to the invention, considering that the process for the manufacture of DCE is advantageously unbalanced (that is to say for example that an external source of HCl makes it possible to provide part of the supply of HCl for the oxychlorination or that a fraction of the DCE produced is not subjected to pyrolysis), the fraction by weight of the throughput of ethylene in each of fractions A and B is advantageously between 20 and 80% of the total quantity of ethylene produced (fraction A+fraction B). Preferably, the fraction by weight of the throughput of ethylene in fraction A is between 25 and 75% of the total quantity of ethylene produced (fraction A+fraction B).

According to a first embodiment of the second subvariant of the preferred variant of the process according to the invention, considering that the process for the manufacture of DCE is advantageously unbalanced by an external source of HCl, the fraction by mole of the throughput of ethylene in fraction A is advantageously between 45 and 55%, preferably between 50 and 54% and in a particularly preferred manner of the order of 52.5% of the difference between the total molar quantity of ethylene contained in the mixture of products subjected to step b) and the molar quantity of HCl of the external source.

According to a second embodiment of the second subvariant of the preferred variant of the process according to the invention, considering that the process for the manufacture of DCE is advantageously unbalanced by a co-production of DCE (some of the DCE is therefore not subjected to pyrolysis), the fraction by mole of the throughput of ethylene in fraction B is advantageously between 45 and 55%, preferably between 46 and 50% and in a particularly preferred manner of the order of 47.5% of the difference between the total molar quantity of ethylene contained in the mixture of products subjected to step b) and the molar quantity of DCE co-produced.

According to the preferred variant of the process of the invention, during step b1), the mixture of products is preferably separated into fraction A, fraction B and into a heavy fraction (fraction C). Fraction C advantageously contains ethane and compounds comprising at least 3 carbon atoms. Advantageously, these compounds comprising at least 3 carbon atoms result from the mixture of products containing ethylene and other constituents derived from step a) or are generated by side reactions during step b1). Among the compounds comprising at least 3 carbon atoms, there may be mentioned propane, propene, butanes and their unsaturated derivatives as well as all the saturated or unsaturated heavier compounds.

Any separation process may be used to separate the mixture of products containing ethylene into fraction A, fraction B and fraction C as long as it advantageously comprises a maximum of four, preferably a maximum of three separation steps in order to obtain both fractions A and B.

According to a first preferred mode of separation, the mixture of products containing ethylene derived from step a) is subjected to a first separation step which makes it possible to extract fraction C therefrom and the resulting mixture is then subjected to a second step for separation into fraction A and fraction B.

According to a second preferred mode of separation, the mixture of products containing ethylene derived from step a) is subjected to a first separation step which makes it possible to extract fraction A therefrom and the resulting mixture is then subjected to a second step for separation into fraction B and fraction C.

The first mode of separation is particularly preferred. Numerous variants can make it possible to carry out this first mode of separation of the mixture of products containing ethylene derived from step a).

A preferred variant of the first mode of separation consists in subjecting the mixture resulting from a first separation step aimed at extracting fraction C, to a second step for separation into fraction A and fraction B which is a distillation step carried out by means of a distillation column equipped with the associative auxiliary equipment such as at least one reboiler and at least one condenser comprising a reflux reservoir. According to this preferred variant, fraction A advantageously leaves at the top of the distillation column and fraction B advantageously leaves at the bottom of the distillation column.

The distillation column may be chosen from plate distillation columns, packed distillation columns, distillation columns with structured packing and distillation columns combining two or more of the abovementioned internals.

The reflux reservoir of the condenser at the top of the column may advantageously serve as a small reservoir for fraction A in case of need. Nevertheless, given that the reservoir B advantageously has a larger storage capacity, it preferably constitutes an ethylene reservoir which can serve to supply the chlorination reactor as a supplement for fraction A while supplying the oxychlorination reactor in addition.

The reservoir B intended to collect fraction B is advantageously placed after the outlet at the bottom of the distillation column. The fraction is advantageously collected therein in the liquid state.

According to a particularly preferred variant, the process according to the invention is therefore characterized in that after step a) and before step d):
b1) the mixture of products containing ethylene is separated into a fraction enriched with the compounds lighter than ethylene containing part of the ethylene (fraction A), into a fraction enriched with ethylene (fraction B) and into a heavy fraction (fraction C);
b2) fraction B is conveyed to a storage reservoir (storage reservoir B or reservoir B); and
c) fraction A is conveyed to a chlorination reactor while fraction B stored in the reservoir B is conveyed to a chlorination reactor and/or an oxychlorination reactor, in which reactors most of the ethylene present is converted to 1,2-dichloroethane.

The specific characteristics detailed above for the preferred variant of the process according to the invention, in particular for fractions A, B and C, the subvariants and the separation process for separating the mixture of products containing ethylene into these three fractions are also applicable for this particularly preferred variant of the process according to the invention.

Given its storage capacity, the reservoir B can, if necessary, advantageously serve to supply, on its own, the chlorination reactor and the oxychlorination reactor.

The chlorination reaction is advantageously performed in a liquid phase (preferably mainly DCE) containing a dissolved catalyst such as $FeCl_3$ or another Lewis acid. It is possible to advantageously combine this catalyst with cocatalysts such as alkali metal chlorides. A pair which has given good results is the complex of $FeCl_3$ with LiCl (lithium tetrachloroferrate—as described in patent application NL 6901398).

The quantities of $FeCl_3$ advantageously used are of the order of 1 to 10 g of $FeCl_3$ per kg of liquid stock. The molar ratio of $FeCl_3$ to LiCl is advantageously of the order of 0.5 to 2.

The chlorination process according to the invention is advantageously performed at temperatures of between 30 and 150° C. Good results were obtained regardless of the pressure both at a temperature less than the boiling temperature (under-cooled chlorination) and at the boiling temperature itself (boiling chlorination).

When the chlorination process according to the invention is a under-cooled chlorination, it gave good results by operating at a temperature which is advantageously greater than or equal to 50° C. and preferably greater than or equal to 60° C., but advantageously less than or equal to 80° C. and preferably less than or equal to 70° C.; with a pressure in the gaseous phase advantageously greater than or equal to 1.5 and preferably greater than or equal to 2 absolute bar, but advantageously less than or equal to 20, preferably less than or equal to 10 and in a particularly preferred manner less than or equal to 6 absolute bar.

A boiling chlorination process is particularly preferred which makes it possible, where appropriate, to usefully recover the heat of reaction. In this case, the reaction advantageously takes place at a temperature greater than or equal to 60° C., preferably greater than or equal to 90° C. and in a particularly preferred manner greater than or equal to 95° C. but advantageously less than or equal to 150° C. and preferably less than or equal to 135° C.; with a pressure in the gaseous phase advantageously greater than or equal to 0.2, preferably greater than or equal to 0.5, in a particularly preferred manner greater than or equal to 1.2 and in a most particularly preferred manner greater than or equal to 1.5 absolute bar but advantageously less than or equal to 10 and preferably less than or equal to 6 absolute bar.

The chlorination process may also be a loop under-cooled boiling mixed chlorination process. The expression loop under-cooled boiling mixed chlorination process is understood to mean a process in which cooling of the reaction medium is performed, for example, by means of an exchanger immersed in the reaction medium or by a loop circulating in an exchanger, while producing in a gaseous phase at least the quantity of DCE formed. Advantageously, the reaction temperature and pressure are adjusted for the DCE produced to leave in the gaseous phase and to remove the remainder of the calories from the reaction medium by means of the exchange surface.

In addition, the chlorination process is advantageously performed in a chlorinated organic liquid medium. Preferably, this chlorinated organic liquid medium, also called liquid stock, mainly consists of DCE.

The fraction A containing the ethylene and the chlorine (itself pure or diluted) may be introduced by any known device into the reaction medium together or separately. A separate introduction of the fraction A may be advantageous in order to increase its partial pressure and facilitate its dissolution which often constitutes a limiting step of the process.

The chlorine is added in a sufficient quantity to convert most of the ethylene and without requiring the addition of an excess of unconverted chlorine. The chlorine/ethylene ratio used is preferably between 1.2 and 0.8 and in a particularly preferred manner between 1.05 and 0.95 mol/mol.

The chlorinated products obtained contain mainly DCE and small quantities of by-products such as 1,1,2-trichloroethane or small quantities of chlorination products of ethane or methane. The separation of the DCE obtained from the stream of products derived from the chlorination reactor is carried out according to known modes and makes it possible in general to exploit the heat of the chlorination reaction.

The unconverted products (methane, carbon monoxide, nitrogen, oxygen and hydrogen) are then advantageously subjected to an easier separation than what would have been necessary to separate pure ethylene starting with the initial mixture.

The oxychlorination reaction is advantageously performed in the presence of a catalyst comprising active elements including copper deposited on an inert support. The inert support is advantageously chosen from alumina, silica gels, mixed oxides, clays and other supports of natural origin. Alumina constitutes a preferred inert support.

Catalysts comprising active elements which are advantageously at least two in number, one of which is copper, are preferred. Among the active elements other than copper, there may be mentioned alkali metals, alkaline-earth metals, rare-earth metals and metals of the group consisting of ruthenium, rhodium, palladium, osmium, iridium, platinum and gold. The catalysts containing the following active elements are particularly advantageous: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium. The catalysts described in patent applications EP-A 255 156, EP-A 494 474, EP-A-657 212 and EP-A 657 213, incorporated by reference, are most particularly preferred.

The copper content, calculated in metal form, is advantageously between 30 and 90 g/kg, preferably between 40 and 80 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are advantageously 1:0.1-2:0.05-2, preferably 1:0.2-1.5:0.1-1.5 and in a particularly preferred manner 1:0.5-1:0.15-1.

Catalysts having a specific surface area, measured according to the B.E.T. method with nitrogen, advantageously between 25 $m^2$/g and 300 $m^2$/g, preferably between 50 and 200 $m^2$/g and in a particularly preferred manner between 75 and 175 $m^2$/g, are particularly advantageous.

The catalyst may be used in a fixed bed or in a fluidized bed. This second option is preferred. The oxychlorination process is exploited under the range of the conditions usually recommended for this reaction. The temperature is advantageously between 150 and 300° C., preferably between 200 and 275° C. and most preferably from 215 to 255° C. The pressure is advantageously greater than atmospheric pressure. Values of between 2 and 10 absolute bar gave good results. The range between 4 and 7 absolute bar is preferred. This pressure may be usefully modulated in order to obtain an optimum residence time in the reactor and to maintain a constant rate of passage for various speeds of operation. The usual residence times range from 1 to 60 seconds and preferably from 10 to 40 seconds.

The source of oxygen for this oxychlorination may be air, pure oxygen or a mixture thereof, preferably pure oxygen. The latter solution, which allows easy recycling of the unconverted reagents, is preferred.

The reagents may be introduced into the bed by any known device. It is generally advantageous to introduce the oxygen separately from the other reagents for safety reasons. These also require maintaining the gaseous mixture leaving the reactor or recycled thereto outside the limits of inflammability at the pressures and temperatures considered. It is preferable to maintain a so-called rich mixture, that is containing too little oxygen relative to the fuel to ignite. In this regard, the abundant presence (>2%, preferably >5% vol) of hydrogen would constitute a disadvantage given the wide range of inflammability of this compound.

The hydrogen chloride (HCl)/oxygen ratio used is advantageously between 3 and 6 mol/mol. The ethylene/hydrogen chloride ratio is advantageously between 0.4 and 0.6 mol/mol.

The chlorinated products obtained contain mainly DCE and small quantities of by-products such as 1,1,2-trichloroethane. The separation of the DCE obtained from the stream of products derived from the oxychlorination reactor is carried out according to known modes. The heat of the oxychlorination reaction is generally recovered in vapour form which can be used for the separations or for any other purpose.

The unconverted products such as methane and ethane are then subjected to an easier separation than that which would have been necessary to separate pure ethylene starting from the initial mixture.

The DCE obtained by chlorination or by oxychlorination of ethylene may then be converted to VC.

The invention also relates to a process for the manufacture of vinyl chloride. To this effect, the invention relates to a process for the manufacture of vinyl chloride, characterized in that the 1,2-dichloroethane obtained by the process according to the invention is subjected to pyrolysis.

The conditions under which the pyrolysis may be carried out are known to persons skilled in the art. This pyrolysis is advantageously obtained by a reaction in the gaseous phase in a tubular oven. The usual pyrolysis temperatures are between 400 and 600° C. with a preference for the range between 480° C. and 540° C. The residence time is advantageously between 1 and 60 s with a preference for the range from 5 to 25 s. The rate of conversion of the DCE is advantageously limited to 45 to 75% in order to limit the formation of by-products and the fouling of the tubes of the oven. The following steps make it possible, using any known device, to collect the purified VC and the hydrogen chloride to be upgraded preferably to the oxychlorination. Following purification, the unconverted DCE is advantageously conveyed to the pyrolysis oven.

In addition, the invention also relates to a process for the manufacture of PVC. To this effect, the invention relates to a process for the manufacture of PVC by polymerization of the VC obtained by the process according to the invention.

The process for the manufacture of PVC may be a mass, solution or aqueous dispersion polymerization process, preferably it is an aqueous dispersion polymerization process.

The expression aqueous dispersion polymerization is understood to mean free radical polymerization in aqueous suspension as well as free radical polymerization in aqueous emulsion and polymerization in aqueous microsuspension.

The expression free radical polymerization in aqueous suspension is understood to mean any free radical polymerization process performed in aqueous medium in the presence of dispersing agents and oil-soluble free radical initiators.

The expression free radical polymerization in aqueous emulsion is understood to mean any free radical polymerization process performed in aqueous medium in the presence of emulsifying agents and water-soluble free radical initiators.

The expression aqueous microsuspension polymerization, also called polymerization in homogenized aqueous dispersion, is understood to mean any free radical polymerization process in which oil-soluble initiators are used and an emulsion of droplets of monomers is prepared by virtue of a powerful mechanical stirring and the presence of emulsifying agents.

One advantage of the process according to the invention consists in the fact that by making it possible to modulate the flow rate of ethylene, it makes it possible to avoid the storage of chlorine and hence the problems of safety linked to it. Indeed, the storage of chlorine would require liquefying this toxic product and would cause a serious risk in case of a leakage. It also makes it possible to avoid the expensive and dangerous storage of HCl gas.

Another advantage of the process according to the invention is that it makes it possible, by virtue of the storage of at least fraction B, to have a lot of flexibility as regards the operation of the chlorination reactor and the oxychlorination reactor.

Thus, in case the chlorination stops, it makes it possible, after appropriate adjustment of the operation of the column, to store the unused ethylene. The light gases (fraction A) depleted of ethylene can find their outlet in a generator. In the case of a stoppage or a variation in the rate of oxychlorination, it also makes it possible to store the unconsumed ethylene or, on the contrary, to satisfy a consumption peak.

Another advantage of the process according to the invention is that it makes it possible to have, on the same industrial site, a completely integrated process from the hydrocarbon source to the polymer obtained starting with the monomer manufactured.

BRIEF DESCRIPTION OF THE DRAWINGS

The process according to the invention will now be illustrated with reference to the drawing accompanying the present description. This drawing consists of the appended FIG. 1, schematically representing one embodiment of the process for the manufacture of 1,2-dichloroethane according to the invention.

The mixture of products 1 containing ethylene and other constituents resulting from the cracking of a hydrocarbon source and of a first separation step which makes it possible to extract the heavy fraction therefrom is introduced into the column 2 which is a distillation column equipped with a reboiler at the bottom and a condenser at the top where it is separated into two different fractions, namely fraction 3 at the top of column 2 and fraction 4 at the bottom of column 2.

Figure 1:
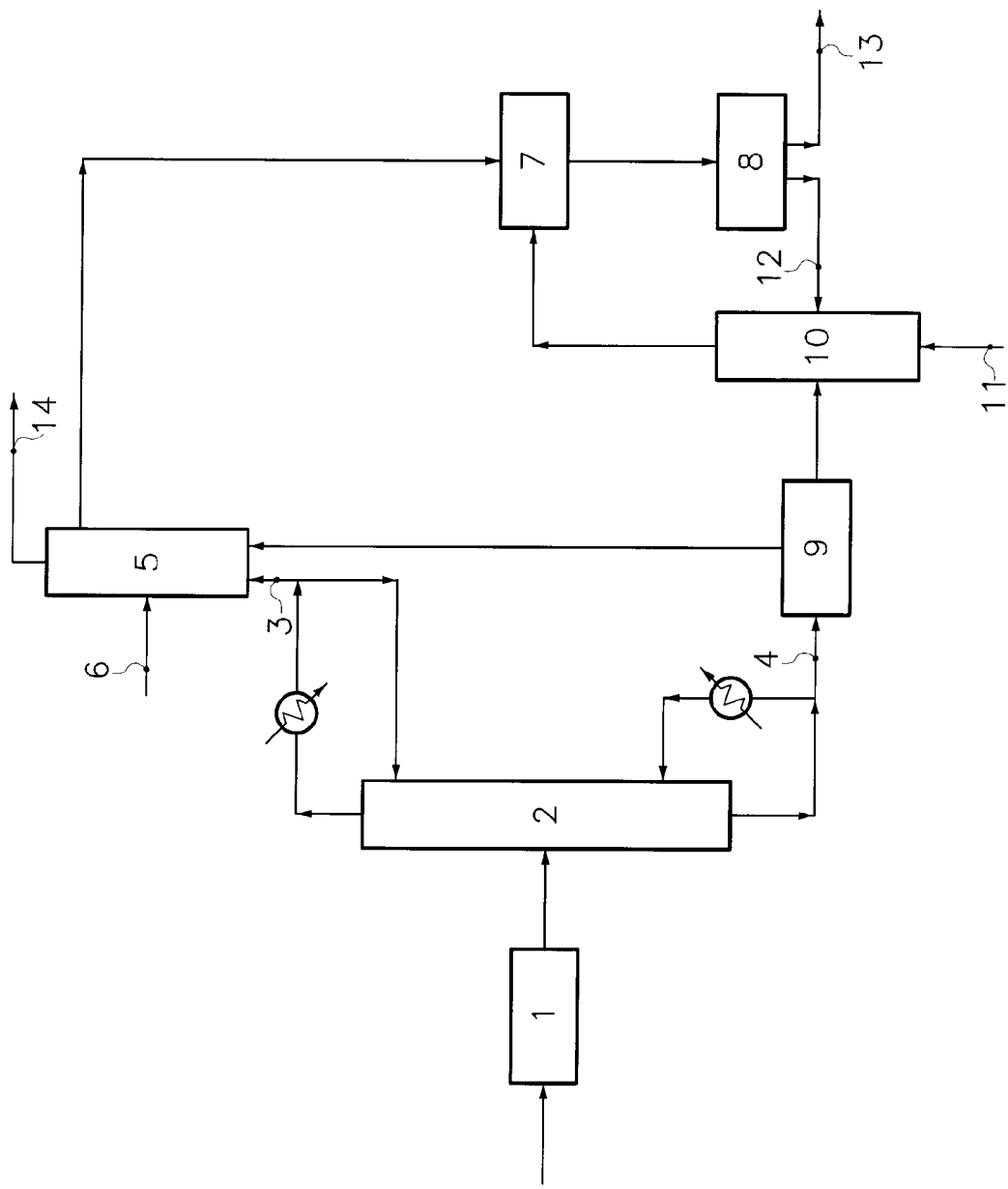

Fraction 3, enriched with compounds lighter than ethylene, in particular methane, hydrogen, nitrogen, oxygen and carbon monoxide, is conveyed to the unit for chlorination of ethylene 5. It is supplied with chlorine 6 whose flow rate is hardly modulable. The DCE formed is conveyed via the sector 7, which comprises any type of purification, to the pyrolysis unit 8.

The liquid fraction 4 characterized by a very low hydrogen content is conveyed to the storage reservoir 9. This ethylene reservoir makes it possible to regulate the flow rate of ethylene to be conveyed to the oxychlorination unit 10 supplied with oxygen or with air 11. The oxychlorination unit receives HCl 12, whose flow rate is hardly modulable, from the pyrolysis unit 8 which produces VC 13. The gases 14 leaving the chlorination unit 5 can be advantageously upgraded as fuels.

According to a preferred embodiment of the process for the manufacture of 1,2-dichloroethane according to the invention, the storage reservoir 9 also partly serves to supply the chlorination unit 5.

The invention claimed is:

1. A process for the manufacture of 1,2-dichloroethane comprising:
    a) cracking a hydrocarbon source to produce a mixture of products comprising ethylene and other constituents;
    b) conveying the mixture of products to at least one storage reservoir;
    c) supplying the previously stored mixture of products to a chlorination reactor and/or an oxychlorination reactor;
    d) converting the ethylene contained in the mixture of products supplied to the chlorination reactor and/or the oxychlorination reactor to 1,2-dichloroethane; and
    e) separating the 1,2-dichloroethane obtained from streams of products derived from the chlorination and/or oxychlorination reactors,
    said process further comprising after a) and before e):
    b1) separating the mixture of products comprising ethylene into a fraction enriched with compounds lighter than ethylene and comprising part of the ethylene (fraction A), into a fraction enriched with ethylene (fraction B) and into a heavy fraction (fraction C);
    b2) conveying fraction A and fraction B to separate storage reservoirs (reservoir A and reservoir B, respectively);
    c1) conveying fraction A stored in reservoir A to a chlorination reactor;
    c2) conveying fraction B stored in reservoir B to a chlorination reactor and/or an oxychlorination reactor,
    d1) converting the ethylene contained in fraction A supplied to the chlorination reactor to 1,2-dichloroethane; and
    d2) converting the ethylene contained in fraction B supplied to the chlorination reactor and/or the oxychlorination reactor to 1,2-dichloroethane.

2. The process for the manufacture of 1,2-dichloroethane according to claim 1, wherein a volume of ethylene relative to the total volume of fraction B is from 40% to 99.5%.

3. The process for the manufacture of 1,2-dichloroethane according to claim 1, wherein a content of ethylene by volume of fraction A is from 10% to 90% of the content by volume of ethylene of fraction B.

4. A process for the manufacture of 1,2-dichloroethane comprising:
    a) cracking a hydrocarbon source to produce a mixture of products comprising ethylene and other constituents;
    b) conveying the mixture of products to at least one storage reservoir;
    c) supplying the previously stored mixture of products to a chlorination reactor and/or an oxychlorination reactor;
    d) converting the ethylene contained in the mixture of products supplied to the chlorination reactor and/or the oxychlorination reactor to 1,2-dichloroethane; and
    e) separating the 1,2-dichloroethane obtained from streams of products derived from the chlorination and/or oxychlorination reactors,
    the process further comprising after a) and before e):
    b1) separating the mixture of products comprising ethylene into:
        a fraction enriched with compounds lighter than ethylene and comprising part of the ethylene (fraction A),
        a fraction enriched with ethylene (fraction B) and
        a heavy fraction (fraction C);
    b2) conveying fraction B to a storage reservoir (storage reservoir B or reservoir B);
    c1) conveying fraction A to a chlorination reactor;
    c2) conveying fraction B stored in the reservoir B to a chlorination reactor and/or an oxychlorination reactor;
    d1) converting the ethylene contained in fraction A supplied to the chlorination reactor to 1,2-dichloroethane; and
    d2) converting the ethylene contained in fraction B supplied to the chlorination reactor and/or the oxychlorination reactor to 1,2-dichloroethane.

5. The process according to claim 1, further comprising pyrolyzing the 1,2-dichloroethane obtained in e) to produce vinyl chloride.

6. The process according to claim 5, further comprising polymerizing the vinyl chloride to produce polyvinyl chloride.

7. The process according to claim 4, further comprising pyrolyzing the 1,2-dichloroethane obtained in e) to produce vinyl chloride.

8. The process according to claim 7, further comprising polymerizing the vinyl chloride to produce polyvinyl chloride.

9. The process for the manufacture of 1,2-dichloroethane according to claim 1, wherein the hydrocarbon source is selected from the group consisting of naphtha, gas oil, natural gas liquid, ethane, propane, butane, isobutane and mixtures thereof.

10. The process according to claim 1, wherein the mixture of products comprising ethylene and other constituents from a) comprises hydrogen, methane, compounds comprising from 2 to 7 carbon atoms, carbon monoxide, nitrogen and oxygen.

11. The process for the manufacture of 1,2-dichloroethane according to claim 4, wherein the hydrocarbon source is selected from the group consisting of naphtha, gas oil, natural gas liquid, ethane, propane, butane, isobutane and mixtures thereof.

12. The process according to claim 4, wherein the mixture of products comprising ethylene and other constituents from a) comprises hydrogen, methane, compounds comprising from 2 to 7 carbon atoms, carbon monoxide, nitrogen and oxygen.

13. The process for the manufacture of 1,2-dichloroethane according to claim 4, wherein a volume of ethylene relative to the total volume of fraction B is from 40% to 99.5%.

14. The process for the manufacture of 1,2-dichloroethane according to claim 4, wherein a content of ethylene by volume of fraction A is from 10% to 90% of the content by volume of ethylene of fraction B.

15. The process for the manufacture of 1,2-dichloroethane according to claim 4, wherein the hydrocarbon source is selected from the group consisting of ethane, propane, butane and a propane/butane mixture.

16. The process for the manufacture of 1,2-dichloroethane according to claim 1, further comprising:
   first separating fraction C from the mixture of products comprising ethylene to obtain a resulting mixture comprising fraction A and fraction B; and then
   separating the resulting mixture into fraction A and fraction B.

17. The process for the manufacture of 1,2-dichloroethane according to claim 4, further comprising:
   first separating fraction C from the mixture of products comprising ethylene to obtain a resulting mixture comprising fraction A and fraction B; and then
   separating the resulting mixture into fraction A and fraction B.

18. The process for the manufacture of 1,2-dichloroethane according to claim 1, further comprising:
   first separating fraction A from the mixture of products comprising ethylene to obtain a resulting mixture comprising fraction C and fraction B; and then
   separating the resulting mixture into fraction C and fraction B.

19. The process for the manufacture of 1,2-dichloroethane according to claim 4, further comprising:
   first separating fraction A from the mixture of products comprising ethylene to obtain a resulting mixture comprising fraction C and fraction B; and then
   separating the resulting mixture into fraction C and fraction B.

20. The process for the manufacture of 1,2-dichloroethane according to claim 1, wherein the hydrocarbon source is selected from the group consisting of ethane, propane, butane and a propane/butane mixture.

* * * * *